US00PP29383P2

(12) United States Plant Patent
Jacobs

(10) Patent No.: US PP29,383 P2
(45) Date of Patent: Jun. 12, 2018

(54) ***CHRYSANTHEMUM* PLANT NAMED 'ZANMUBRIWHI'**

(50) Latin Name: ***Chrysanthemum×morifolium* Ramat.**
Varietal Denomination: Zanmubriwhi

(71) Applicant: Chrysanthemum Breeders Association Research BV, Valkenburg ZH (NL)

(72) Inventor: Henricus Cornelius Maria Jacobs, Valkenburg (NL)

(73) Assignee: Van Zanten Breeding B.V., Rijsenhout (NL)

( * ) Notice: Subject to any disclaimer, the term of this patent is extended or adjusted under 35 U.S.C. 154(b) by 38 days.

(21) Appl. No.: 15/530,244

(22) Filed: Dec. 16, 2016

(51) Int. Cl.
*A01H 5/02* (2018.01)

(52) U.S. Cl.
USPC ..... Plt./294

(58) Field of Classification Search
USPC ..... Plt./294
See application file for complete search history.

*Primary Examiner* — Keith O Robinson
(74) *Attorney, Agent, or Firm* — Steptoe & Johnson LLP

(57) ABSTRACT

A *chrysanthemum* plant named 'Zanmubriwhi' characterized by its medium sized blooms with white ray florets and prolific branching; natural season flowering date September 12; blooming for a period of 5 weeks.

3 Drawing Sheets

Botanical designation: *Chrysanthemum×morifolium* Ramat.

Cultivar denomination: 'Zanmubriwhi'.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmubriwhi'. 'Zanmubriwhi' is a product of a breeding and selection program for outdoor pot mums (garden mums) which had the objective of creating new cultivars with a white double type inflorescence, a natural season flowering date around September 12, blooming for a period of 5 weeks. 'Zanmubriwhi' is a seedling resulting from a cross of the female parent 9375 (unpatented) with the male parent 57947 (unpatented). Plants of the new cultivar 'Zanmubriwhi' differ from plants of the female parent in the follow characteristics. (1) Ray-floret color and (2) Natural season blooming date. (1) Ray-florets are yellow in the female parent plant, and white in the new plant. (2) Plants of the female parent flower one week earlier than those of the new plant. Plants of the new cultivar 'Zanmubriwhi' differ from plants of the male parent in the following characteristics. (1) Plant size and (2) Natural season blooming date. (1) Plants of the male parent are smaller than those of the new plant. (2) Plants of the male parent flower one week earlier than those of the new plant.

The new and distinct cultivar was discovered and selected as a flowering plant by Henricus Cornelius Maria Jacobs on a cultivated field in Rijsenhout, The Netherlands in week 37 2012. The first act of asexual production of 'Zanmubriwhi' was accomplished when vegetative cuttings from the initial selection were propagated further in a controlled environment in Rijsenhout, the Netherlands. In summer, about 6-8 days are needed to initiate roots in cuttings of the new cultivar, after another 5 days rooted plants are formed. The new cultivar has been found to retain its distinctive characteristics through successive propagations.

BRIEF DESCRIPTION OF THE DRAWINGS

The present invention of a new and distinct variety of *chrysanthemum* (of about 16 weeks) is shown in the accompanying drawings, the color being as nearly true as possible with color photographs of this type.

DESCRIPTION OF THE INVENTION

Figure 1:
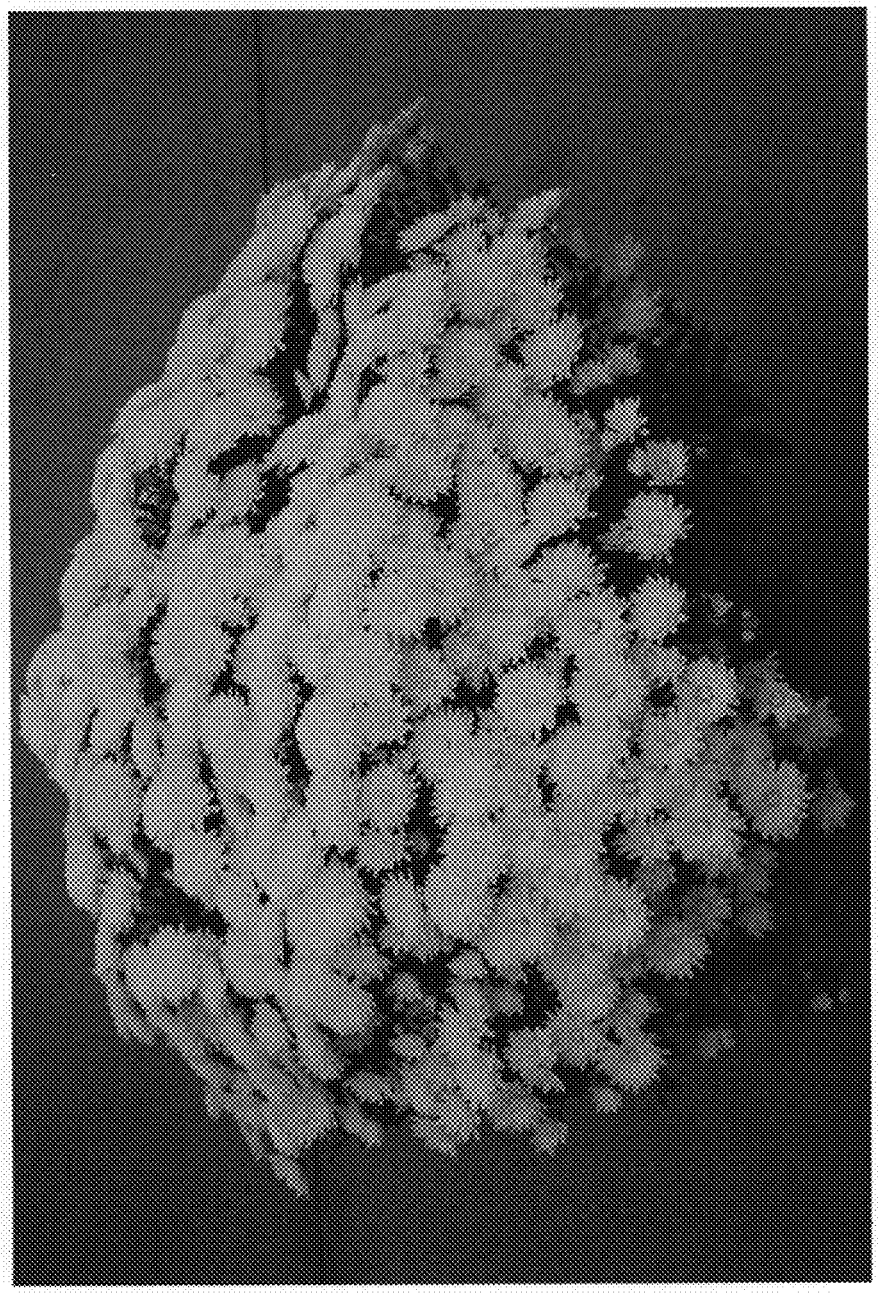
FIG. 1 shows a plant of the cultivar in full bloom.
Figure 2:
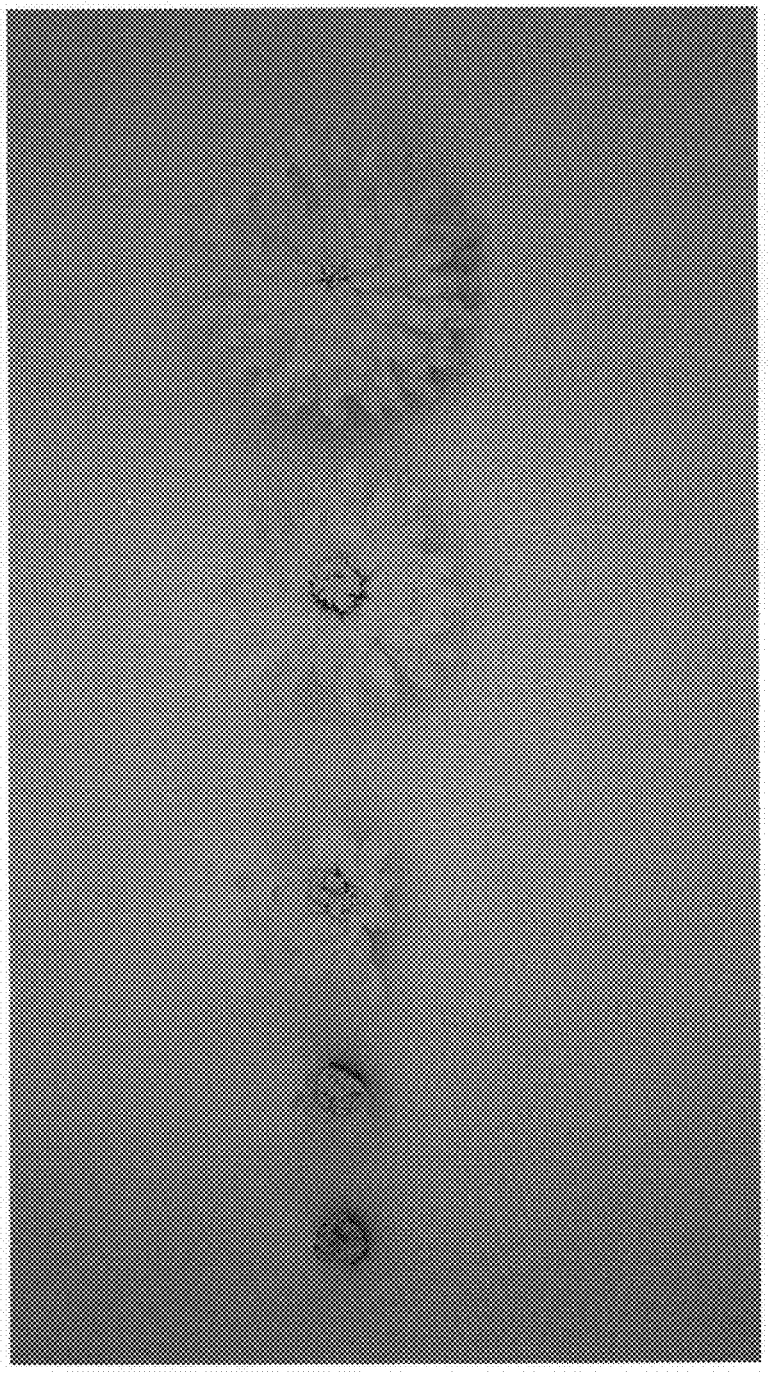
FIG. 2 shows the various stages of bloom of the new cultivar.
Figure 3:
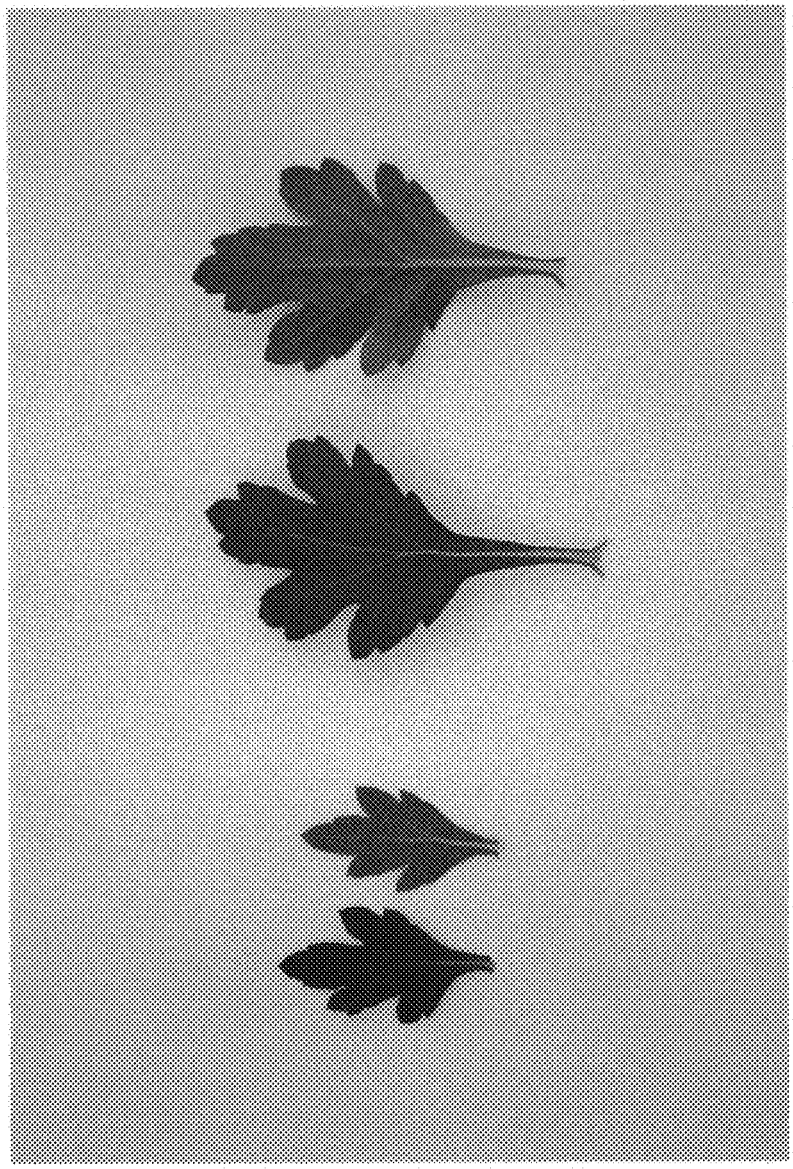
FIG. 3 shows the various stages of foliage of the new cultivar.

The observations and measurements were gathered from plants in the period of 13 to 19 weeks of age grown outdoor in Rijsenhout, the Netherlands, under natural day length and temperature and planted in week 23 in 2016, receiving drip irrigation. The natural blooming date of this crop was September 12. The average height of the plants was 40 cm. No growth retardants were used. No tests were done on disease or insect resistance or susceptibility. No tests were done on cold or drought tolerance. This new variety produces medium sized blooms with white ray florets blooming for a period of 5 weeks.

From the cultivars known to the inventor the most similar existing cultivar in comparison to 'Zanmubriwhi' is 'Zanmuspen' (U.S. Plant Pat. No. 21,205). When 'Zanmuspen' and 'Zanmubriwhi' are being compared the following differences are noticed (1) Flower color and (2) Plant vigor. (1) The flowers of 'Zanmubriwhi' are more white than those of 'Zamuspen'. (2) Plants of 'Zanmubriwhi' are more vigorous than those of 'Zanmuspen'.

The following is a description of the plant and characteristics that distinguish 'Zanmubriwhi' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, sixth edition (2015).

Table 1. Botanical Description of *Chrysanthemum×morifolium* Ramat. 'Zanmubriwhi'.

Bud:
- *Size*.—Small; cross-section 6 mm, height 4 mm.
- *Shape*.—Round.
- *Texture*.—Pubescent.
- *Outside color*.—Greyed-green 191B.

Phyllaries:
- *Number*.—24, arranged in 3 rows.
- *Shape*.—Elliptic.
- *Apex*.—Acute.
- *Base*.—Truncate.
- *Margin*.—Entire.
- *Color*.—Upper side: Green 135A. Lower side: Greyed-green 189A.
- *Length and width*.—4 mm; 1.5 mm.
- *Texture*.—Pubescent.

Inflorescences:
- *Type*.—Double.
- *Height*.—1.8-2 cm.
- *Diameter*.—5.5-6 cm.
- *Peduncle length*.—5.5-8 cm.
- *Peduncle color*.—Green 138C.
- *Peduncle diameter*.—1.5 mm.
- *Peduncle texture*.—Pubescent.
- *Number per branch*.—About 6 inflorescences.
- *Duration of flowering*.—5 weeks.
- *Seeds*.—Produced in small quantities, ovate, Greyed-brown 199A, length 1.5 mm, diameter 0.5 mm; texture: rough with ribs.
- *Fragrance*.—Faint *chrysanthemum* odor.

Color inflorescences:
- *Center of inflorescence*.—Immature stage: Yellow 8C; Mature stage: Yellow 8C.
- *Color of upper side of ray florets*.—Outer rows: White NN155B; Inner Rows: Yellow 8D.
- *Color of lower side of ray florets*.—Outer rows: White 155D; Inner rows: Yellow 8D.
- *Tonality from distance*.—A garden mum with white blooms and a cream center.
- *Color of ray florets after aging of the plant*.—White 155D.

Ray florets:
- *Number of types*.—2.
- *Type*.—Outer rows: Ligulate; Inner Rows: Quilled.
- *Texture*.—Upper and lower side smooth.
- *Number*.—230-240.
- *Shape*.—Outer rows: Elliptic; Inner rows: Narrowly elliptic.
- *Apex*.—Dentate.
- *Base*.—Attenuate.
- *Cross-section*.—Outer rows: Concave; Inner rows: Circular.
- *Longitudinal axis*.—Outer rows: Straight; Inner rows: Incurving.
- *Length of corolla tube outer row*.—7-30 mm.
- *Diameter corolla tube outer row*.—1 mm.
- *Ray floret margin*.—Entire.
- *Ray floret length*.—Outer rows: 2.5-4 cm: Inner rows: 1-1.6 cm.
- *Ray-floret width*.—Outer rows: 3-5 mm; Inner rows: 1.5 mm.
- *Ratio length/width*.—Medium (outer rows) and High (inner rows).

Disc florets: Absent.

Receptacle:
- *Color*.—Yellow-green 145D.
- *Shape*.—Domed raised.
- *Height*.—5 mm.
- *Diameter*.—8 mm.

Reproductive organs:
- *Androecium*.—Absent.
- *Pollen*.—Lacking.
- *Gynoecium*.—Present on ray florets.
- *Style color*.—Yellow-green 154C.
- *Style length*.—4 mm.
- *Stigma color*.—Yellow 7A.
- *Stigma width*.—1 mm.
- *Ovary*.—Enclosed in calyx.
- *Ovary color*.—Yellow-green 149D.

Plant:
- *Type*.—Bushy.
- *Growth habit*.—Spherical shape.
- *Growth rate*.—Vigorous.
- *Height*.—40 cm.
- *Width*.—55 cm.
- *Stem color*.—Greyed-brown 199A.
- *Stem strength*.—Medium.
- *Stem brittleness*.—Brittle.
- *Stem anthocyanin coloration*.—Absent.
- *Internode length*.—0.4-2 cm.
- *Length of lateral branch*.—From top to bottom 12-18 cm.
- *Lateral branch color*.—Green 138A.
- *Lateral branch, attachment*.—Medium.
- *Lateral branch diameter*.—3.5. mm.
- *Lateral branch, texture*.—Pubescent with ribs.
- *Branching* (*average number of lateral branches*).—Dense with 8-9 breaks after pinching.
- *Natural season blooming date*.—September 12 (week 37) in Rijsenhout, the Netherlands.
- *Roots*.—Habits: Fine, freely branching.
- *Roots*.—Color: White 155A.

Foliage:
- *Glossiness*.—Leaf upper side: weak. Leaf lower side: weak.
- *Leaf color*.—Upper side: Green 136A. Lower side: Green N138A.
- *Color midvein*.—Upper side: Yellow-green 147D. Lower side: Yellow-green 148D.
- *Size*.—Small; length 2-5.5 cm, width 1.4-3 cm.
- *Quantity* (*number per lateral branches*).—26-30.
- *Shape*.—Elliptic.
- *Texture upper side*.—Sparsely pubescent.
- *Texture under side*.—Pubescent.
- *Venation arrangement*.—Pinnate.

*Shape of margin*.—Serrated.

*Shape of base of sinus between lateral lobes*.—Acute.

*Margin of sinus between lateral lobes*.—Diverging.

*Shape of base*.—Attenuate to Truncate.

*Apex*.—Mucronulate.

*Petiole strength*.—Weak.

*Petiole attitude*.—Strongly upwards.

*Petiole length*.—0.2-1.5 cm.

*Petiole diameter*.—1.5 mm.

*Petiole color*.—Yellow-green 147D.

*Stipules*.—Small.

TABLE 2

| Differences with the comparison variety, when grown under identical conditions | | |
|---|---|---|
| | 'Zanmubriwhi' | 'Zanmuspen' |
| Flower color | White NN155B with Yellow 8C center | White 155A with Yellow 10A center |
| Plant vigor | High | Medium |

I claim:

1. A new and distinct *chrysanthemum* plant named 'Zanmubriwhi' as described and illustrated.

* * * * *